United States Patent
Kuo et al.

(10) Patent No.: US 6,607,382 B1
(45) Date of Patent: Aug. 19, 2003

(54) METHODS AND SYSTEMS FOR CONCURRENT TOOTH REPOSITIONING AND SUBSTANCE DELIVERY

(75) Inventors: Eric Kuo, San Francisco, CA (US); Loc X. Phan, Milpitas, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 09/666,783

(22) Filed: Sep. 21, 2000

(51) Int. Cl.⁷ .................................................. A61C 3/00
(52) U.S. Cl. ............................. 433/6; 433/80; 433/216
(58) Field of Search ............................. 433/6, 80, 215, 433/216

(56) References Cited

U.S. PATENT DOCUMENTS

| | | |
|---|---|---|
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,860,803 A | 1/1975 | Levine |
| 3,922,786 A | 12/1975 | Lavin |
| 3,950,851 A | 4/1976 | Bergersen |
| 4,253,828 A | 3/1981 | Coles et al. |
| 4,324,546 A | 4/1982 | Heitlinger et al. |
| 4,324,547 A | 4/1982 | Arcan et al. |
| 4,447,164 A * | 5/1984 | Berndt |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,591,341 A | 5/1986 | Andrews |
| 4,609,349 A | 9/1986 | Cain |
| 4,664,626 A | 5/1987 | Kesling |
| 4,676,747 A | 6/1987 | Kesling |
| 4,755,139 A | 7/1988 | Abbatte et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,936,862 A | 6/1990 | Walker et al. |
| 4,941,826 A | 7/1990 | Loran et al. |
| 4,968,251 A * | 11/1990 | Darnell .......................... 433/216 |

(List continued on next page.)

FOREIGN PATENT DOCUMENTS

| | | |
|---|---|---|
| FR | 2369828 | 6/1978 |
| WO | WO 94/10935 | 5/1994 |
| WO | WO 98/32394 | 7/1998 |
| WO | WO 98/58596 | 7/1998 |

OTHER PUBLICATIONS

Andrews, "The Six Keys to Optimal Occlusion" *Straight Wire*, Chapter 3 pp13–24.

Biostar Opeation & Training Manual. Great Lakes Orthodontics, Ltd. 199 Fire Trower Drive, Tonawanda, New York. 14150–5890. 20 pages total.

(List continued on next page.)

*Primary Examiner*—Ralph A. Lewis
(74) *Attorney, Agent, or Firm*—Townsend and Townsend and Crew LLP; Bao Tran, Esq.

(57) ABSTRACT

The present invention provides devices, systems and methods for orthodontic treatment using elastic repositioning appliances while concurrently providing dental and periodontal therapies. Such therapies are traditionally provided with the use of a variety of accessories and devices which are applied when the repositioning appliance is removed from the patient's mouth. The present invention eliminates the need for such removal and additional devices by incorporating these therapies into the repositioning appliance.

45 Claims, 9 Drawing Sheets

U.S. PATENT DOCUMENTS

| | | | |
|---|---|---|---|
| 4,983,334 A | | 1/1991 | Adell |
| 4,990,089 A | * | 2/1991 | Munro ........................ 433/215 |
| 5,011,405 A | | 4/1991 | Lemchen |
| 5,017,133 A | | 5/1991 | Miura |
| 5,035,613 A | | 7/1991 | Breads et al. |
| 5,055,039 A | | 10/1991 | Abatte et al. |
| 5,059,118 A | | 10/1991 | Breads et al. |
| 5,085,585 A | * | 2/1992 | Zimble ........................ 433/80 |
| 5,100,316 A | | 3/1992 | Wildman |
| 5,125,832 A | | 6/1992 | Kesling |
| 5,127,903 A | * | 7/1992 | Mailot et al. .................. 604/77 |
| 5,139,419 A | | 8/1992 | Andreiko et al. |
| 5,145,364 A | | 9/1992 | Martz et al. |
| 5,165,424 A | * | 11/1992 | Silverman ................... 128/861 |
| 5,186,623 A | | 2/1993 | Breads et al. |
| 5,273,429 A | | 12/1993 | Rekow et al. |
| 5,338,198 A | | 8/1994 | Wu et al. |
| 5,340,309 A | | 8/1994 | Robertson |
| 5,342,202 A | | 8/1994 | Deshayes |
| 5,367,478 A | | 11/1994 | Hattori |
| 5,368,478 A | | 11/1994 | Andreiko et al. |
| 5,382,164 A | | 1/1995 | Stern |
| 5,395,238 A | | 3/1995 | Andreiko et al. |
| 5,431,562 A | | 7/1995 | Andreiko et al. |
| 5,447,432 A | | 9/1995 | Andreiko et al. |
| 5,452,219 A | | 9/1995 | Dehoff et al. |
| 5,454,717 A | | 10/1995 | Andreiko et al. |
| 5,456,600 A | | 10/1995 | Andreiko et al. |
| 5,474,448 A | | 12/1995 | Andreiko et al. |
| 5,528,735 A | | 6/1996 | Strasnick et al. |
| 5,533,895 A | | 7/1996 | Andreiko et al. |
| 5,542,842 A | | 8/1996 | Andreiko et al. |
| 5,549,476 A | | 8/1996 | Stern |
| 5,587,912 A | | 12/1996 | Anderson et al. |
| 5,605,459 A | | 2/1997 | Kuroda et al. |
| 5,607,305 A | | 3/1997 | Andersson et al. |
| 5,645,420 A | * | 7/1997 | Bergersen ....................... 433/6 |
| 5,645,421 A | | 7/1997 | Slootsky |
| 5,683,243 A | | 11/1997 | Andreiko et al. |
| 5,692,894 A | | 12/1997 | Schwartz et al. |
| 5,725,376 A | | 3/1998 | Poirier |
| 5,725,378 A | | 3/1998 | Wang |
| 5,800,174 A | | 9/1998 | Andersson |
| 5,846,058 A | * | 12/1998 | Fischer ........................ 433/216 |
| 5,866,058 A | | 2/1999 | Batchelder et al. |
| 5,879,158 A | | 3/1999 | Doyle et al. |
| 5,880,961 A | | 3/1999 | Crump |
| 5,924,863 A | * | 7/1999 | Jacobs et al. .................. 433/80 |
| 5,957,686 A | | 9/1999 | Anthony |
| 5,964,587 A | | 10/1999 | Sato |
| 5,971,754 A | | 10/1999 | Sondhi et al. |
| 5,975,893 A | * | 11/1999 | Chishti et al. ................ 433/80 |
| 6,044,309 A | | 3/2000 | Honda |
| 6,049,743 A | | 4/2000 | Baba |
| 6,068,475 A | * | 5/2000 | Stoyka, Jr. ................... 433/80 |
| 6,089,869 A | * | 7/2000 | Schwartz .................... 433/215 |
| 6,123,544 A | | 9/2000 | Cleary |
| 6,183,248 B1 | | 2/2001 | Chishti et al. |
| 6,190,165 B1 | | 2/2001 | Andreiko et al. |
| 6,217,334 B1 | | 4/2001 | Hultgren |
| 6,293,790 B1 | * | 9/2001 | Hilliard ........................ 433/4 |

OTHER PUBLICATIONS

Chiappone, "Constructing the gnathologic setup and positioner" *J. Clin. Orthod.* (1980) 14:121–133.

Cottingham, "Gnathologic clear plastic positioner" *Am. J. Orthod.* (1969) 55:23–31.

Cureton, "Correcting malaligned mandibular incisors with removable retainers" *J. Clin. Orthod.* (1996) 30:390–395.

Dent–X posted at http://www.dent–x.com/DentSim.htm Sep. 24, 1998, 6 pages total.

Elsasser, "Some observations on the history and uses of the Kesling positioner" *Am. J. Orthod.* (1950) 36:368–374.

Kamada et al., "Case reports on tooth positioners using LTV vinyl silicone rubber" *J. Nihon University School of Dentistry* (1984) 26(1):11–29.

Kamada et al., "Construction of tooth positioners with LTV vinyl silicone rubber and some case reports" *J. Nihon University School of Dentistry* (1982) 24(1):1–27.

Kesling, "Coordinating the predetermined pattern and tooth positioner with conventional treatment" *Am. J. Orthod. Oral. Surg.* (1946) 32:285–293.

Kesling, "The philosophy of the tooth positioning appliance" *Am. J. Orthod. Oral. Surg.* (1945) 31(6):297–304.

Kleemann et al., "The speed positioner" *J. Clin. Orthod.* (1996) 30:673–680.

Kunii et al., "Articulation Simulation for an Intelligent Dental Care System" *Displays* (1994) 15:181–188.

Kuroda et al., "Three–dimensional dental cast analyzing system using laser scanning" *Am. J. Orthod. Dentofac. Orthop.* (1996) 110:365–369.

Nahoum et al., "The vacuum formed dental contour appliance" *The New York State Dental Journal* (1964) 30(9):385–390.

*Nippon Dental Review* "New orthodontic device–dynamic positioner (D.P.)–I. Approach to the proposal of D.P. and transparent silicone rubber" (1980) 452:61–74.

*Nippon Dental Review* "New orthodontic device–dynamic positioner (D.P.)–II. Practical application and construction of D.P." (1980) 454:107–130.

*Nippon Dental Review* "New orthodontic device–dynamic positioner (D.P.)–III. Case reports of reversed occlusion" 1980) 457:146–164.

*Nippon Dental Review* "New orthodontic device–dynamic positioner (D.P.)–Case reports of reversed occlusion" (1980) 458:112–129.

Nishiyama et al., "A new construction of tooth repositioner by LTV vinyl silicone rubber" *J. Nihon University School of Dentistry* (1977) 19(2):93–102.

Cardinal Industrial Finishes, Powder Coatings information posted at http://www.cardinalpaint.com on Aug. 25, 2000, 2 pages total.

Proffit et al, "Contemporary Orthodontics" Second Edition, Chapter 15, pp 470–533.

Raintree Essix™ & ARS Materials, Inc., Raintree Essix™ Technical Magazine Table of Contents and Essix™ Applications, http://www.essix.com/magazine/default.html (Aug. 13, 1997) 7 pages total.

Richmond et al., "The development of the PAR Index (Peer Assessmetn Rating): reliability and validity" *European Journal of Orthodontics* (1992) 14:125–139.

Schroeder et al., Eds. *The Visual Toolkit*, Prentice Hall PTR, New Jersey (1998) Chapters 6,8, and 9 (pp. 153–210, 309–354, and 355–428, respectively).

Shilliday, "Minimizing finishing problems with the mini–positioner" *Am. J. Orthod.* (1971) 59:596–599.

Warunek et al., "Clinical use of silicone elastomer applicances" *JCO* (1989) XXIII(10):694–700.

Warunek et al., "Physical and mechanical properties of elastomers in orthodontic positioners" *Am. J. Orthod. Dentofac. Orthop.* (1989) 95:388–400.

Wells, "Application of the positioner appliance in orthodontic treatment" *Am. J. Orthodont.* (1970) 58:351–366.

* cited by examiner

METHODS AND SYSTEMS FOR CONCURRENT TOOTH REPOSITIONING AND SUBSTANCE DELIVERY

BACKGROUND OF THE INVENTION

The present invention is related generally to the field of medical methods and devices. More particularly, the present invention is related to the oral delivery of substances concurrently with the realignment of teeth.

Orthodontic treatments involve repositioning misaligned teeth and improving bite configurations for improved cosmetic appearance and dental function. Repositioning is accomplished by applying gentle controlled forces to the teeth over an extended period of time. Due to the limited space within the oral cavity and extensive movements that some teeth must undergo, the teeth will often be moved throughout a series of intermediate patterns to properly arrange the teeth. For example, molars may be temporarily moved backwards (distalized) to create adequate space for movement of the incisors. Thus, a single patient may experience an average of 25–30 stages or alignment patterns before achieving the final desired configuration.

Recently, it has been found that such repositioning may be accomplished with the use of a series of removable elastic positioning appliances. Such appliances comprise a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances comprising new configurations eventually move the teeth through a series of intermediate configurations or alignment patterns to a final desired configuration. A full description of an exemplary elastic polymeric positioning appliance is described in U.S. Pat. No. 5,975,893, and in published PCT application WO 98/58596 which designates the United States and which is assigned to the assignee of the present application. Both these documents are incorporated by reference for all purposes.

In addition to their ease of use, polymeric positioning appliances are generally transparent and impart substantial force on the teeth, due to stiffness of the appliance. The stiffness of an elastic positioning appliance is a result of the modulus of the thermoformable polymer materials from which it is made. The higher the modulus of the materials, the higher the stiffness of the appliance. When a patient positions such an appliance over a prescribed group of teeth, one or more of the teeth will provide a base or anchor region for holding the positioning appliance in place while the stiffness of the polymeric material will impart a resilient repositioning force against one or a portion of the remaining teeth. By designing the appliance to cover the teeth, a much larger contact surface area is afforded compared to traditional spring retainers and wire-based appliances.

As described, the appliances are only effective in repositioning teeth when the appliance is placed over the patient's teeth. Removal of the appliance for any reason interrupts the treatment plan and lengthens the overall period of treatment. Therefore, removal of the appliance should be minimized for effective and timely treatment. However, a number of dental and periodontal therapies which may be desired or required by the patient may not be effectively utilized while the appliance is in place. Such therapies may be prescribed by a practitioner to improve oral health or they may be requested by the patient for cosmetic purposes.

Oral health concerns often include tooth decay, gingivitis, and periodontitis, to name a few. Tooth decay may be largely prevented or arrested with fluoride treatment. Treatments include toothpastes, gels, rinses and varnishes. Gum disease, such as gingivitis or periodontitis, is caused by bacterial growth associated with dental plaque and calculus deposits. The most common recommendation for preventing such bacterial growth is to mechanically remove the plaque from the tooth surfaces. However, chronic gingivitis and tooth decay have plagued many individuals who in fact comply with good oral hygiene methods and plaque removal. This may be due to a variety of factors including genetic predispositions, illnesses, mouth breathing, and medical treatment programs.

In such cases, bacterial control may be accomplished with the use of antibacterial drugs. A common antibacterial agent shown to be effective in reducing the activity of many common strains of oral flora is chlorhexidine. Chlorhexidine is a cationic biguanide microbicide with a broad spectrum of activity against many forms of bacteria and fungi. Therefore, it has been a popular agent in many studies of gingivitis reversal. Chlorhexidine has traditionally been delivered to the oral environment through the use of rinses, such as Peridex® (Proctor and Gamble). Sustained delivery to the gingiva has also been attempted with the use of chlorhexidine impregnated dental floss and dental appliances, such as trays or mouthguards.

Another frequently prescribed antibacterial agent is tetracycline. Tetracycline is a broad spectrum antibiotic which is effective against virtually all common groups of pathogenic bacteria, both gram positive and negative. Tetracycline may be combined with an antifungal agent, such as amphotericin, to provide activity against fungi. Tetracycline has traditionally been delivered to the oral environment through systemic administration, although localized delivery has been attempted with the insertion of tetracycline-filled hollow fiber devices into periodontal pockets and the use of tetracycline laden dental appliances, such as trays and mouthguards. In addition, a number of other antibacterial drugs are available for dental and periodontal therapy.

Cosmetic treatments often include tooth bleaching or whitening and breath freshening products. Discolorations of enamel and dentin may occur due to aging, consumption of staining substances (coffee, tea, colas, tobacco), trauma, staining due to systemic tetracycline (antibiotic) therapy, excessive fluoride, nerve degeneration and old dental restorations. Bleaching lightens these discolorations for a whiter or brighter appearance. Typically, a bleaching gel is placed in a thin custom-fitted tray that fits over the teeth. The tray is worn at night for usually 10 to 14 days and may require periodic re-bleaching treatments for approximately one or two nights every six months. Breath freshening products are often used by patients to treat halitosis or for enjoyment of the taste. These include a variety of sprays, rinses, mints, gums, or candies, to name a few.

Many of these therapies require access to the teeth and gingival margin which are typically covered by the elastic repositioning appliance when in use. In addition, some of these therapies may best be administered by localized delivery over extended periods of time which would create substantial interruption of the treatment plan. For example, low level delivery of antibiotics by sustained release methods is often desired to treat periodontal disease. Likewise, treatments such as bleaching and whitening may require interruption of the treatment plan for up to two weeks. Removal of the appliance during these periods would lengthen the overall treatment period. In addition, many of these therapies require the usage of specific devices, gels, rinses, applicators and instructions for each administration of therapy. These accessories may be costly, bulky and difficult to use.

Although removal of the appliance should be minimized, it is necessary to remove the appliance during daily oral hygiene routines, such as brushing and flossing of the teeth. Likewise, the appliance may be removed from time to time for participation in athletic activities or for comfort, such as when eating. The ability to temporarily remove such appliances allows the patient to pursue conventional oral hygiene, but teeth which are covered by the appliances a majority of the time may still be at an increased risk of dental and periodontal disease.

It would be desirable to provide improved devices, systems and methods utilizing elastic repositioning appliances which permit and/or enhance concurrent dental and periodontal therapies. Likewise, it would be desirable to provide such devices, systems and methods which would reduce or eliminate the need for additional accessories and/or protocols to apply such therapies. Further, the devices, systems and methods should be economical and easy to use. At least some of these objectives will be met by the designs and methods of the present invention described hereinafter.

SUMMARY OF THE INVENTION

The present invention provides devices, systems and methods for orthodontic treatment using repositioning appliances, typically elastic polymeric shells, while concurrently delivering substances to the teeth or gums, for example, to provide dental and periodontal and/or cosmetic therapies. Such therapies are traditionally provided with the use of a variety of accessories and devices which are applied using separate appliances, materials, etc. The present invention eliminates the need for such additional devices by incorporating these therapies into the repositioning appliance. Moreover, the ability to deliver therapeutic and other agents is concurrent with the course of a repositioning procedure.

By "concurrent" or "concurrently," it is meant that the substance or agent delivery to the teeth occurs during at least a portion of the duration of the repositioning of the teeth. Thus, the substance may be delivered continuously during the entire duration of the repositioning process, i.e. the substance may be present in or on each repositioning appliance in an amount or amounts sufficient to assure that it is released to the oral environment at all times the appliance is placed over the teeth. Alternatively, the substance may be present in or on the repositioning appliance(s) at only selected times or over selected time intervals so that the substances are delivered at spaced-apart times during the repositioning process. For example, each successive repositioning appliance may be preloaded with a bolus of the substance so that the bolus is delivered to the patient at the outset of use of each new appliance. After the initial bolus is depleted, the substance will not be delivered again until the next successive appliance is used. As an alternative example, the patient could apply an amount of a substance at a time each day, where the substance is then released over a relatively short time interval and no more substance delivered until the next day. A multitude of other particular patterns are also possible.

While the appliances will be particularly intended for repositioning teeth, most often when used in systems of multiple aligners, t hey may in some instances be useful as drug or substance delivery devices without the concurrent repositioning of teeth. In particular, many of the specific device constructions described below are themselves novel and useful for substance delivery, and the present invention encompasses such devices.

In a first aspect of the present invention, an oral delivery appliance comprises an elastic repositioning appliance providing one or more substances or agents for oral delivery. As previously described, elastic repositioning appliances comprise a thin shell of elastic polymeric material having cavities shaped to receive and resiliently reposition teeth from one arrangement to a successive arrangement. This is possible because the cavities are shaped to fit a mold of digitally arranged teeth in the successive arrangement. A full description of an exemplary elastic repositioning appliance shaped in this manner is described in U.S. Pat. No. 5,975,893, and in published PCT application WO 98/58596. Placement of the elastic positioner over the teeth applies controlled forces in specific locations to gradually move the teeth into the new configuration. In order to apply sufficient force, the appliance generally covers the tooth surfaces and portions of the gingival margin. Thus, both individual repositioning appliances and systems of such elastic repositioning devices may be used to deliver agents to the underlying tooth surfaces and gingiva comprising the oral environment while repositioning teeth.

In a first embodiment, the oral delivery appliance delivers fluoride to the oral environment to prevent or treat tooth decay. Traditionally, fluoride has been delivered to the oral environment through the use of toothpastes, gels, rinses and varnishes, to name a few. The present invention provides fluoride delivery which may be used in conjunction with traditional applications or may replace certain applications. Such fluoride may be provided in a number of forms, such as neutral sodium fluoride, stannous fluoride, hydrogen fluoride, or acidulated phosphate fluoride (APF) gel, for example. Fluoride may be releasably attached to the elastic repositioning appliance in a number of forms, as will be described in more detail in later sections, to provide delivery to the oral environment.

In a second embodiment, the oral delivery appliance delivers an antibiotic or drug to the oral environment. In the case of antibiotics, delivery of such an agent may inhibit or kill various microorganisms. Antibiotics often used to treat gingivitis and periodontitis include chlorhexidine and tetracycline. Such antibiotics may be releasably attached to the elastic repositioning appliance in a number of forms, as will be described in more detail in later sections, to provide delivery to the oral environment.

In a third embodiment, the oral delivery appliance delivers a bleaching material to the oral environment. Bleaching of the teeth is a common cosmetic procedure requested of dental practitioners by their patients. The active ingredient in standard bleaching gels is carbamide peroxide and is typically present in an 18–37% suspension. Bleaching materials, such as carbamide peroxide, may be releasably attached to the elastic repositioning appliance in a number of forms, as will be described in more detail in later sections, to provide delivery to the oral environment.

In a fourth embodiment, the oral delivery appliance delivers a breath freshener to the oral environment. Breath fresheners are commonly available in a number of flavors and scents, including mint and fruit flavors, derived from essential oils and/or natural or artificial flavorings, to name a few. Such breath fresheners may be releasably attached to the elastic repositioning appliance in a number of forms, as will be described in more detail in later sections, to provide delivery to the oral environment.

In a second aspect of the present invention, at least some of the elastic repositioning appliances in a system for repositioning teeth are coupled to means for releasing the agent to the oral environment when the appliance is placed over the teeth. Such means may comprise a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be comprised of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may comprise the agent present in or on a carrier or binder which promotes adhesion or attachment to the appliance and/or which creates a matrix from which the agent can be released by diffusion or dissolution. In one embodiment, the agent is dissolved in the carrier or binder. In this case, the agent may be provided in powder or similar form and dissolved in a liquid solvent. The result may be a solution which may be applied to a surface of the shell, typically by spraying, painting and/or dipping, to form a coating or film. When the repositioning appliance is placed over the patient's teeth, the agent may then be released from the coating to the oral environment. Release may be due to activation or deactivation of the carrier or any other releasing mechanism, such as by enzymes or proteins in saliva. Or release may be due to degradation of the carrier by contact with, for example, saliva. In some cases, the binder or carrier may evaporate upon application to the layer to the surface leaving the agent behind. In these cases, the agent may be released in a similar fashion as when the agent is directly attached to the surface, as described above. It may be appreciated that any agent, particularly fluoride materials, antibiotics, bleaching materials and breath fresheners, may be delivered to the oral environment in this manner.

In another embodiment, the agent is encapsulated or suspended in the layer. A common material for suspension of an agent is a semisolid material, such as a gel, jelly or putty. Such a material may be applied to a surface of the shell by spraying, painting and/or dipping to form a coating or film. Here, as in all cases, suspension is not limited to a scientific definition and may refer to any situation in which a carrier holds, contains, supports or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials and breath fresheners, may be delivered to the oral environment in this manner.

Another common material for encapsulation or suspension of an agent is a controlled-release material. Thus, the layer may be comprised of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly or putty, as described above, these materials may also be provided as a solid material which is attached to the polymeric shell of the repositioning appliance. One type of controlled-release material comprises a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, enzymes in the patient's saliva will activate the release or degrade the carrier material to release the agent. It may be appreciated that the agent may be released by a combination of any of the release methods.

In a further embodiment, the polymeric shell of the repositioning appliance itself comprises a controlled-release material containing the agent. In this case, at least a portion of at least some of the polymeric shells in a system for repositioning teeth are formed from a controlled release material wherein the rate controlling material controls the rate at which the agent is released from the shell. As previously described, the controlled-release material may be a provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In a still further embodiment, the releasing means coupled to at least some of the repositioning appliances comprises a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or pre-loaded with an agent or substance for delivery. In this case, the appliance may be ready for insertion or use upon removal from any packaging without the need of loading the appliance with the agent for delivery. If the releasing means is designed for a single delivery period, the appliance may be worn throughout the prescribed repositioning period and then disposed of. If the releasing means is designed for multiple delivery periods, the reservoir may be replenished with the agent to be released any number of times throughout the prescribed repositioning period. It may be appreciated that any agent, particularly fluoride materials, antibiotics, bleaching materials and breath fresheners, may be delivered to the oral environment in this manner.

In some instances, it may be desirable to change a visual characteristic of the polymeric shell of an oral appliance. Such appliances comprise a polymeric shell having a cavity shaped to be removably placeable over the teeth and a material on or within the shell that changes a visual characteristic of the shell. Such a change is typically in response to a change in the environment. In some cases, the visual characteristic is a color, such as green, red or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37° C.) to room temperature (25° C.). Similarly, the dye may change color when the appliance is rinsed with cool water.

In a fourth aspect of the present invention, methods for concurrently repositioning teeth and delivering agents to the oral environment of a patient are provided. For example, one method comprises placing a first tooth position adjustment appliance over the patient's teeth, wherein the teeth move to a first tooth arrangement. After removal of the first appliance, a second tooth position adjustment appliance is placed over the patient's teeth wherein the teeth move to a second tooth arrangement. Concurrently with the repositioning of the teeth, an agent or substance is released from at least one of the first and second tooth position adjustment appliances to the oral environment while the appliance is in place of the patient's teeth.

Although the appliance may be pre-loaded with the agent and ready for use upon removal from any packaging, appliances that are not pre-filled or pre-loaded may require loading prior or immediately prior to placing the appliance over the teeth. Loading may comprise placing the agent in a teeth-receiving cavity. As described previously, the cavities may be filled to any desired level. When the appliance is positioned over the teeth, the teeth will directly contact the agent in the cavities as the teeth are inserted into the cavities. Alternatively, loading may comprise placing the agent into an agent release reservoir in the appliance immediately prior to placing the appliance over the teeth. The agent will then elute from the reservoir into the oral environment when the appliance is in place over the teeth. The elution rate may be controlled by a controlled release membrane which separates the reservoir from the surrounding environment. Loading may also comprise adhering a rate controlling material containing the agent to a surface of the appliance prior to placing the appliance over the teeth. Such a material may comprise a polymer matrix membrane which may be removably or permanently adhered to the polymeric shell of the appliance in desired areas for delivery of the agent. And finally, loading may comprise absorbing the agent into a porous material on or within the appliance immediately prior to placing the appliance over the teeth.

Repositioning of the teeth with the use of a position adjustment appliance involves placing the appliance over the teeth. However, the appliance is periodically removed for daily dental hygiene practices and other events throughout the repositioning protocol until the teeth are moved to at least near the desired tooth arrangement. While the appliance is removed from the teeth, the appliance may be replenished with the agent or substance for delivery. Replenishment may be performed immediately prior to each time the appliance is replaced over the teeth or it may be performed according to any prescribed protocol.

In a fifth aspect of the present invention, methods for introducing agent delivery to a prescribed tooth repositioning treatment plan are provided. A treatment plans is determined by an orthodontist or practitioner at the outset of orthodontic treatment. The plan involves moving the teeth through a series of intermediate configurations or arrangements to a final desired arrangement with the use of a system of tooth positioning appliances. Each appliance comprises a polymeric shell having cavities which is removably placeable over the teeth and wherein the cavities of successive shells are shaped to reposition teeth from one arrangement to a successive arrangement according to the treatment plan. The entire series of appliances may be provided at the outset of treatment, or a subset of appliances. In any case, the need or desire for delivery of an agent to the oral environment may occur at any point during the course of treatment. In such a case, an agent and/or means for releasing an agent to the oral environment may be coupled to an appliance at any time during treatment.

Means for releasing the agent may include a number of embodiments, including any such means previously described. Typically, means for releasing the agent comprises a layer including the agent, as previously described, and coupling comprises adhering the layer to at least a portion of a surface of the appliance. When the layer consists essentially of the agent, adhering may involve coating, spraying, dipping or painting the agent on the surface of the appliance. Thus, a pre-formed appliance may simply be coated with the agent prior to insertion in the patient's mouth. When the layer comprises an agent present in or on a carrier or binder, adhering may involve attaching the carrier or binder a surface of the appliance. Similarly, when the agent is encapsulated in the layer, the layer may be attached to the surface of the appliance. The layer may comprise a sheet of rate controlling material wherein the rate controlling material controls the rate at which the agent is released from the layer. In this case, the sheet may be bonded to the surface of the appliance with an adhesive. Alternatively, the sheet may be attached to the surface by press fitting. The sheet and the surface may each be shaped so that they snap or fit together by pressing them together. For example, the sheet may have a formed protrusion and the surface a formed inset, wherein the protrusion fits into the inset when pressed upon the inset and holds the sheet in place. In many instances, the appliance may be porous or have a reservoir which can be loaded with a desired agent at any time the treating professional and/or the patient decide that it is appropriate. For example, an appliance can be immersed in a solution f the agent, allowing the appliance to absorb or adsorb the agent at a particular time.

In addition, the sheet may be pre-formed to a shape adapted for fitting against the surface of the appliance or a surface of the teeth or gingiva. For example, the sheet may be pre-formed to reflect the shape of the surface of one or more teeth or the gingiva, particularly along the gingival margin. The preformed sheet may then be held against that surface when the sheet is coupled to the appliance and the appliance is placed over the teeth. Coupling may involve any means of attaching the sheet to the appliance. In particular, the pre-formed sheet may further comprise an adhesive layer which may provide bonding of the sheet to the surface of the appliance.

Other objects and advantages of the present invention will become apparent from the detailed description to follow, together with the accompanying drawings.

DESCRIPTION OF THE SPECIFIC EMBODIMENTS

Figure 1:
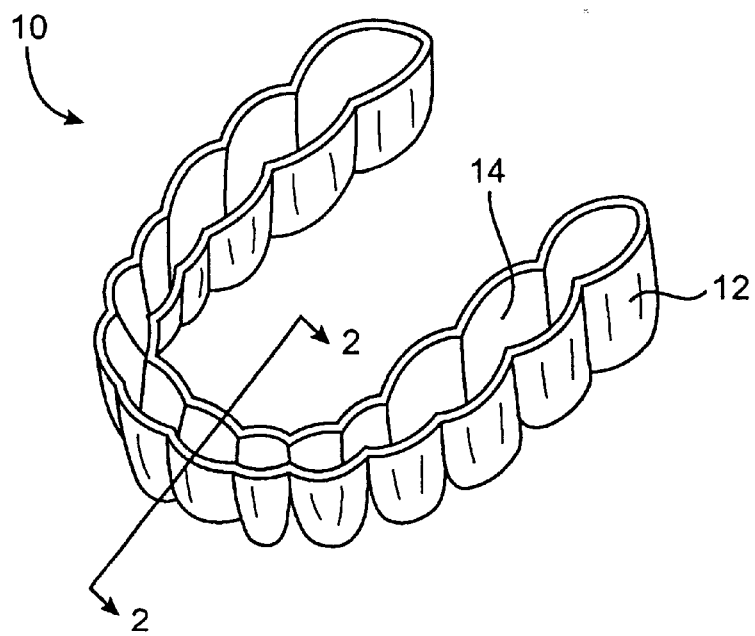
FIG. 1 is a schematic illustration of an exemplary elastic repositioning appliance.

An oral delivery appliance of the present invention comprises an elastic repositioning appliance which concurrently provides orthodontic repositioning forces and dental therapies. FIG. 1 depicts an exemplary elastic repositioning appliance 10 used for orthodontic treatment. The appliance 10 comprises a polymeric shell 12 having cavities 14 shaped to receive and resiliently reposition teeth from one tooth arrangement to a successive tooth arrangement. The appliance 10 is preferably formed from a thin sheet of a suitable elastomeric polymer, such as Tru-Tain 0.03 in. thermal forming dental material (Tru-Tain Plastics, Rochester, Minn.), or Essix A-Type or Essix B-Type thermal forming material (Raintree-Essix, New Orleans, La.). The overall method for producing incremental position adjustment is provided in U.S. Pat. No. 5,975,893, previously incorporated by reference. But, in general, the shell 10 is typically produced by heating a thermoformable polymer sheet and vacuum or pressure forming the sheet over tooth members of a mold. Thus, the shell 12 is a direct representation of the characteristics of the mold. If this appliance 10 is worn by a patient as a stage in orthodontic repositioning, the shell 12 will preferably, but not necessarily, fit over all teeth or dental features supported by the patient's dental arch. Those teeth which are to be repositioned will be slightly misfit by the appliance to allow force and movement into the desired positions.

Dental and periodontal therapies may be simultaneously delivered by such an elastic repositioning appliance to provide uninterrupted orthodontic treatment while treating other conditions. Such therapies include fluoride treatment to prevent or treat tooth decay, antibiotic or drug therapy to treat gingivitis and periodontitis, bleaching to improve the cosmetic appearance of the teeth, and/or breath freshening to treat halitosis. In addition, such an elastic repositioning appliance may also comprise a material which changes a visual characteristic of the shell in response to a change in the environment, as stated previously.

Each of the above identified therapies involves one or more therapeutic agents which are delivered to the oral environment. The present invention provides a tooth positioning appliance coupled to means for releasing one or more of these agents to the oral environment. Agents for the above identified therapies include, but are not limited to, various forms of fluoride, such as neutral sodium fluoride and stannous fluoride, various antibiotics, such as chlorhexidine and tetracycline, bleaching ingredients, such as carbamide peroxide, and breath fresheners or flavors. Means for releasing the agent may include a number of embodiments.

Figure 2:
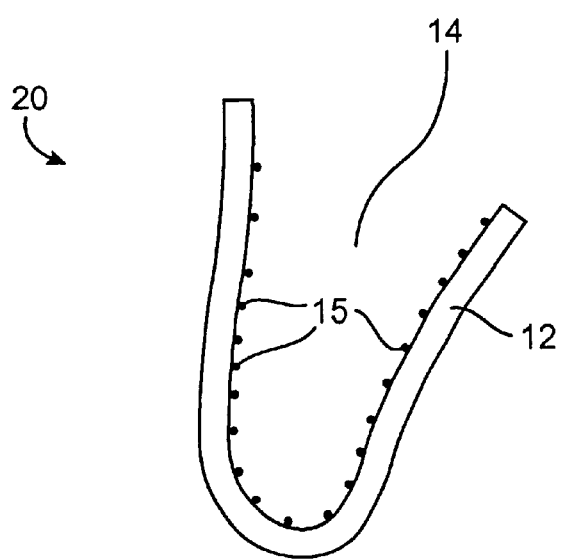
FIG. 2 is a cross-sectional view along line 2—2 of the repositioning appliance of FIG. 1 with a layer comprising an agent on its surface.

In one embodiment, means for releasing the agent to the oral environment comprises a layer including the agent formed over at least a portion of the surfaces of the polymer shell. Such a layer may comprise the agent 15 itself. This is illustrated in FIG. 2, which depicts a cross-sectional view (along line 2—2 of FIG. 1) of a polymer shell 12 having cavities 14, shaped to receive and resiliently reposition teeth, and an agent 15 attached to its surface. It may be appreciated that the depictions of the agent is for illustration purposes and does not necessarily reflect the actual shape, size relationship or distribution of the agent particles. This applies to all depictions of agents hereinafter. Such attachment or formation of the layer may be achieved by applying the agent 15 to the surface of the shell 12 by a number of methods, including spraying, painting and/or dipping. Thus, when the oral delivery appliance 20 is placed over the patient's teeth, the agent may then be released to the oral environment. When the agent 15 is attached to the inside surface of the appliance 20, as shown in FIG. 2, the agent may directly contact the teeth and/or gingiva. This may be best suited for treatments such as fluoride or antibiotic therapy which benefit from direct contact with the teeth and/or gingiva. However, other treatments, such as breath freshening, may most benefit from attachment to the outer surface of the appliance 20. Therefore, agents 15 may be attached to any or all surfaces of the appliance 20.

Figure 3:
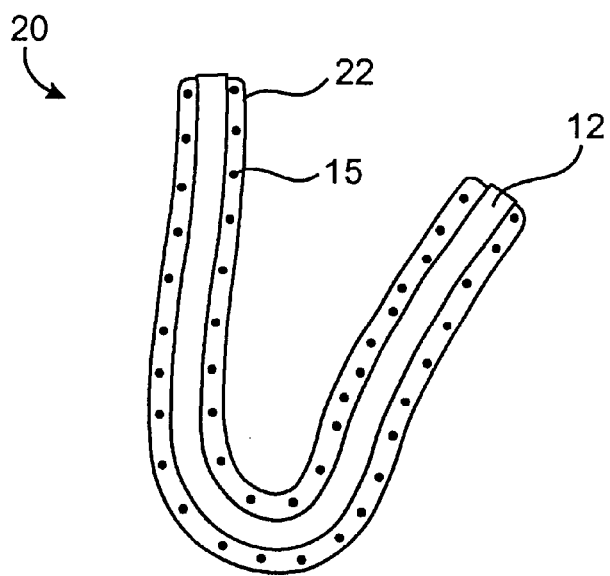
FIG. 3 is a cross-sectional view of an appliance having a semisolid material containing an agent applied to its surface.
Figure 4:
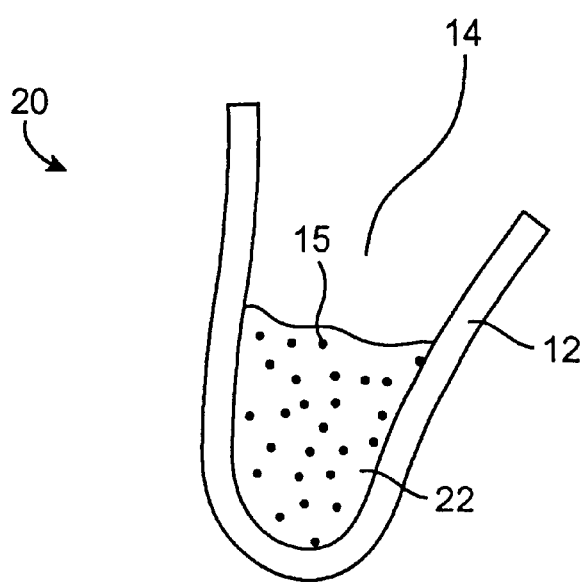
FIG. 4 is a cross-sectional view of an appliance having a cavity filled with a semisolid material containing an agent.

In another embodiment, the layer comprises the agent 15 present in a carrier or binder. A common carrier for suspension of an agent is a semisolid material, such as a gel, jelly or putty. As depicted in FIG. 3, such semisolid material 22 may be applied to the surface of the shell 12 by spraying, painting and/or dipping to form a coating or film. Alternatively, as depicted in FIG. 4, the semisolid material 22 may be deposited in the cavities 14 of the polymer shell 12 which are shaped to receive the teeth. The cavities 14 may be filled to any desired level such that when the appliance 20 is positioned over the teeth, the teeth will directly contact the material 22 and displace any extra material 22. Delivery of an agent 15 by the use of such a material 22 is most common in bleaching and fluoride treatments, however any type of agent 15 may be used.

Another type of layer is a controlled-release material impregnated with the agent, wherein the rate controlling material controls the rate at which the agent is released from the layer. Controlled-release or rate-controlled materials deliver an agent at a predetermined rate. As previously described, such delivery may be achieved by a number of methods. First, the agent may be released by diffusion through the controlled-release material. In this case, the agent is typically present as finely dispersed particles in a polymer matrix membrane. This is often termed a monolithic dispersed type system, monolithic device, or matrix diffusion system. As the concentration of agent is reduced in the matrix due to diffusion delivery to the oral environment, the slope of the drug diffusion curve is also reduced. The agent delivery rate decreases over time as the material is depleted. Hence, the characteristic release profile of a monolithic system follows an asymptotic curve; after an initial burst of rapid release, the elution approaches a constant rate. Second, the agent may be released by degradation of the controlled-release material. Degradation may be achieved by a number of mechanisms, including enzymatic degradation by enzymes in the saliva. The agent may be encapsulated or contained in a biodegradable material, such as a polymer matrix. Any number of degradation rates may be achieved by manipulating the molar ratio of the monomers in the matrix. Further, the agent may be released by a combination of diffusion and degradation of the releasing layer. Alternatively or in addition, the agent may be released by elution from pores within the releasing layer. Depending on the structure of the layer, elution from the pores may be achieved by a number of methods. If the agent is contained in a controlled-release material which fills the pores, the agent may be released from the controlled-release material by diffusion and/or degradation and then elution from the pores themselves.

Figure 5:
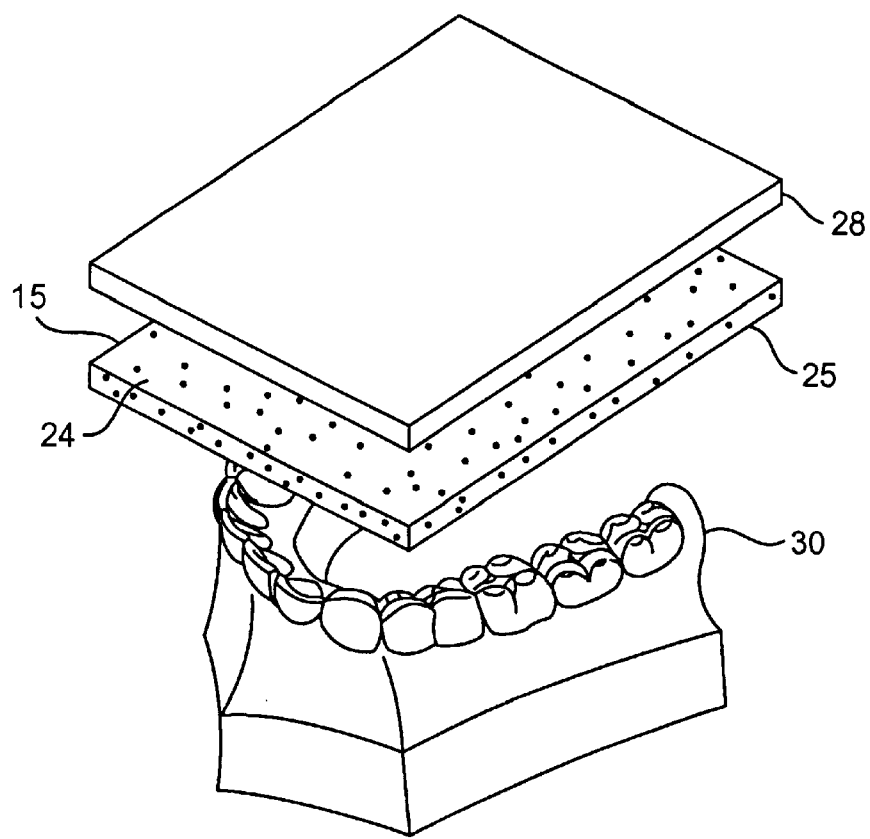
FIG. 5 illustrates the layering of a sheet of controlled-release material containing an agent with a polymeric sheet for use in the formation of an oral delivery appliance.

One attribute of controlled-release materials is that they may be provided in a solid form, such as a thin film or sheet, which may be attached to the polymeric shell of an elastic repositioning appliance. Referring to FIG. 5, a controlled-release material 24 containing the agent 15 may be provided as a sheet 25 and used in the formation of an appliance of the present invention. Here, the sheet 25 may be layered with an elastomeric polymer sheet 28 over a mold 30 of the patient's dentition. Together the sheets 25, 28 may be vacuum formed over the mold 30 to form the repositioning appliance. By placing the controlled-release material sheet 25 between the mold 30 and the polymer sheet 28, as shown, the controlled-release material 24 will cover the inside surfaces of the appliance and will be positioned against the patient's teeth and/or gums when the appliance is in place. This may be most beneficial for elution of agents 15 such as fluoride, antibiotics or bleaching materials.

Figure 6:
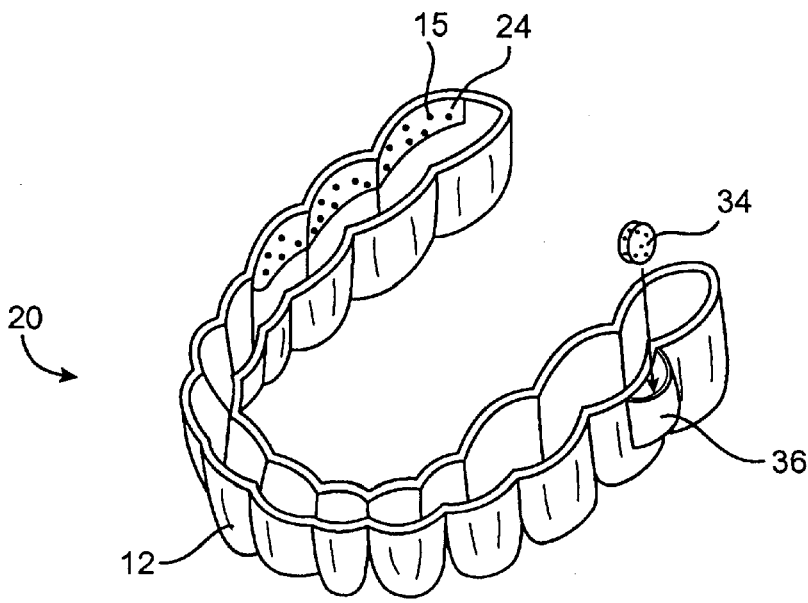
FIG. 6 illustrates the attachment of a controlled-release material to the polymeric shell of an appliance and the insertion of a controlled-release tablet into a portion of the polymeric shell.

Alternatively, the controlled-release material 24 may be attached to the polymeric shell 12 of the oral delivery appliance 20 after forming the appliance. As shown in FIG. 6, the controlled-release material 24 containing the agent 15 may be laminated, bonded or otherwise attached to a surface of the polymer shell 12 in a desired area. Such attachment may be removable, so that the material 24 may be removed when the agent 15 has substantially eluted or the therapy is to be discontinued, or it may be non-removable, so that the material 24 is present throughout the life of the appliance. Also shown in FIG. 6 is the use of a controlled-release tablet 34 which may be inserted into a pocket 36 or portion of the polymeric shell 12 of the appliance 20. Portions of the pocket may be perforated or meshed to facilitate delivery of the agent. The agent may then elute from the tablet 34 into the oral environment over time. This design may be most applicable to elution by degradation of the tablet 34, wherein the tablet 34 may be replaced periodically for renewed delivery.

In a further embodiment, the releasing means comprises a reservoir formed in the polymer shell in addition to the cavity which receives the teeth. Reservoir devices or membrane diffusion systems can supply an agent or substance at a constant rate under sink conditions. These systems consist of three elements: a reservoir containing the agent, a low concentration sink, such as the oral environment, and a rate-controlling membrane separating the reservoir from the sink. The system obeys Fick's Law of Diffusion for the mass flux across the membrane. Thus, the system is held at a constant delivery rate based on the diffusion coefficient through the membrane.

Figure 7:
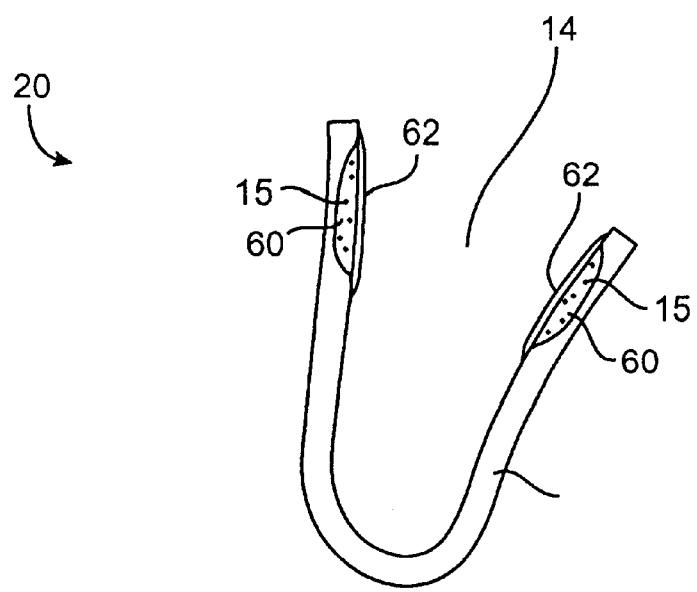
FIG. 7 illustrates a reservoir type releasing means having sealed ends.
Figure 8:
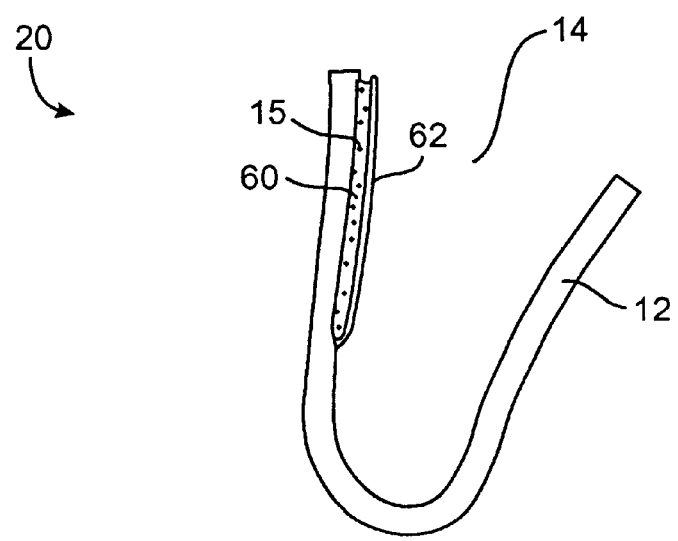
FIG. 8 illustrates a reservoir type releasing means that is accessible to the user so that the reservoir may be replenished with an agent.

Referring to FIG. 7, the releasing means is shown to comprise a reservoir 60 formed in the polymer shell 12, in addition to the cavity 14 which receives the teeth. The reservoir holds the agent 15 and is covered by a rate controlling membrane 62 which controls the rate at which the agent 15 is released from the reservoir 60. The reservoirs 60 are depicted as being located substantially within the wall of the polymer shell 12 for elution to the cavity 14. However, it may be appreciated that reservoirs 60 may be located anywhere in the shell 12, may be external to the wall of the shell 12 and may elute in any direction. The reservoirs 60 may be pre-filled with the agent 15 to be released. That is, the appliance 20 is provided with the reservoirs 60 filled with the agent 15. In this case, the reservoirs 60 may be sealed by the membrane 62 as depicted in FIG. 7. However, the reservoirs 60 may also be accessible to the user so that the reservoir may be replenished with agent 15 as desired. In this case, the reservoir 60 may be not be sealed by the membrane 62 as depicted in FIG. 8.

Figure 9:
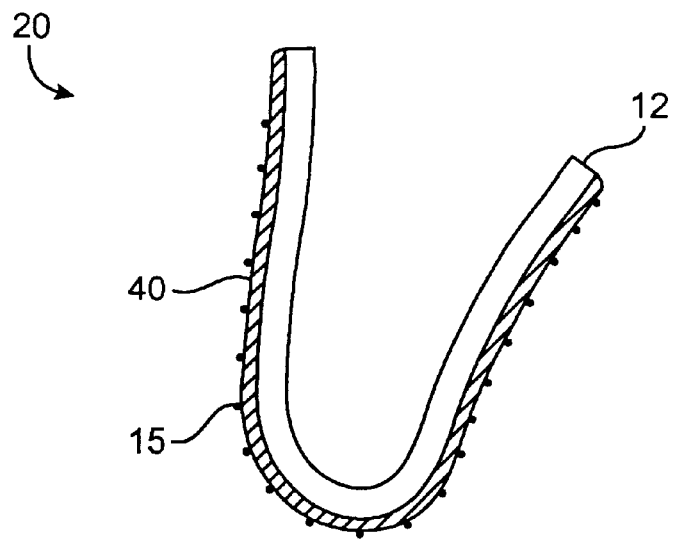
FIG. 9 is a cross-sectional view of an appliance having a binding material and releasably bound agent applied to its surface.

In another embodiment, the agent 15 is supported by a carrier. As depicted in FIG. 9, the carrier comprises a binding material 40 which releasably binds the agent 15 to a surface of the polymeric shell 12. The binding material 40 may release the agent 15 by a number of mechanisms, including dissolution of the binding material 40, activation or deactivation of the binding material 40 or any other release mechanism.

Figure 10:
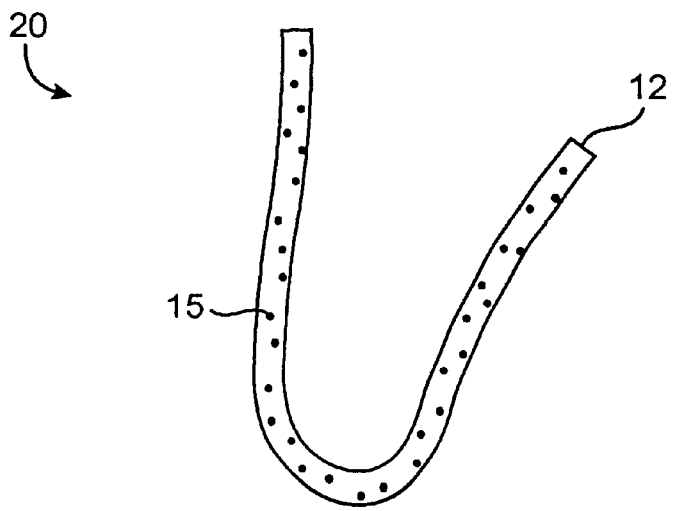
FIG. 10 is a cross-sectional view of an appliance comprised of a controlled-release material containing an agent.

In a further embodiment, as depicted in FIG. 10, the polymeric shell 12 of the oral delivery appliance 20 is comprised of a controlled-release material 42 containing an agent 15. In this case, the controlled-release material 42 itself is formed to function as a repositioning appliance. This may be achieved by vacuum forming a sheet of controlled-release material over a mold of the patient's teeth. The agent 15 may then elute from the appliance 20 by means of diffusion or other release mechanisms.

Means for releasing the agent to the oral environment have been described in a number of embodiments, above, in regards to the agent itself. However, in each embodiment, the agent may first be encapsulated or microencapsulated in a material, typically a polymer. Such encapsulation may be desired or necessary to protect the agent from the effects of processing. For example, some agents may be hydrolyzed or denatured by processes such as extrusion or thermoforming which may be involved in the production of the appliance. Encapsulation may also protect the agent from environmental factors throughout the shelf-life of the appliance. Therefore, in the above descriptions and throughout, "agent" may identify the agent itself or an encapsulated agent.

Agents may be encapsulated or entrapped by a number of materials. Such materials may include polylactic acids, polycapric lactones, polyvinyl alcohols, polyacrylic acids, polyethylene oxides, polylactide glycolic biodegradable polymer capsules and side-chain crystalizable polymers, to name a few. Encapsulation may be achieved by a variety of processes. Particularly, the agent may be encapsulated by spray-drying. For example, the agent may be mixed or combined with a solvent, such as polyvinyl alcohol, and then combined with a polymer resin. After the solvent evaporates, polymer microcapsules, each containing the agent dispersed throughout its matrix, are retained.

The encapsulating or entrapping material may or may not provide controlled-release of the agent from the microsphere. If the encapsulating material does provide controlled-release capabilities, such a layer would be in addition to any controlled-release means for releasing the agent previously described. For example, the encapsulated agent may be dispersed throughout a sheet of controlled-release material which is later attached to the polymeric shell of an elastic repositioning appliance. When the appliance is positioned in the patient's mouth, the agent may elute at a controlled rate based on the release of the agent from the encapsulating material and from the sheet of controlled-release material.

Similarly, the encapsulating material may be an ion exchange resin. Such resins have a very high surface area and are able to absorb a large quantity of an agent for controlled-delivery. An exemplary resin is sold under the trademark MICROSPONGE (Advanced Polymer Systems), and described, for example, in U.S. Pat. No. 5,145,675, the full disclosure of which is incorporated herein by reference. In addition to serving as an encapsulating material, ion exchange resins may be used for as a controlled-delivery material in any of the above described embodiments.

Figure 11:
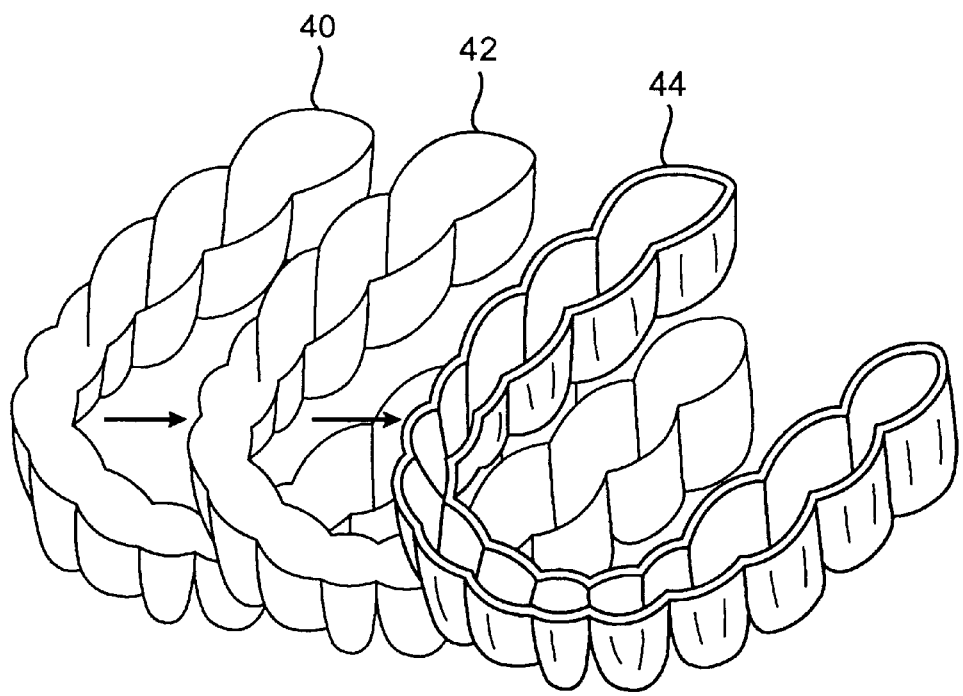
FIG. 11 illustrates a gradual color change of an appliance from transparent to colored as the appliance changes in temperature.

In some instances it may be desirable to change a visual characteristic of the polymeric shell of an oral appliance. Such appliances comprise a polymeric shell 12 having a cavity 14 shaped to be removably placeable over the teeth and a material on or within the shell that changes a visual characteristic of the shell. Such a change is typically in response to a change in the environment. For example, the material may be a dye which changes color when the appliance is removed from the patient's mouth and changes temperature due to the change in environment. This gradual color change is illustrated in FIG. 11. For example, as shown, a transparent oral delivery appliance 40 will remain transparent when it is in the mouth and maintained at body temperature. Upon removal from the mouth, the appliance will cool to room temperature. As the appliance begins to cool, the colorant will gradually become visible, as illustrated in the tinted oral delivery appliance 42. As the appliance equilibrates to room temperature, the colorant will become more visible, as illustrated in the colored oral delivery appliance 44.

Figure 12:
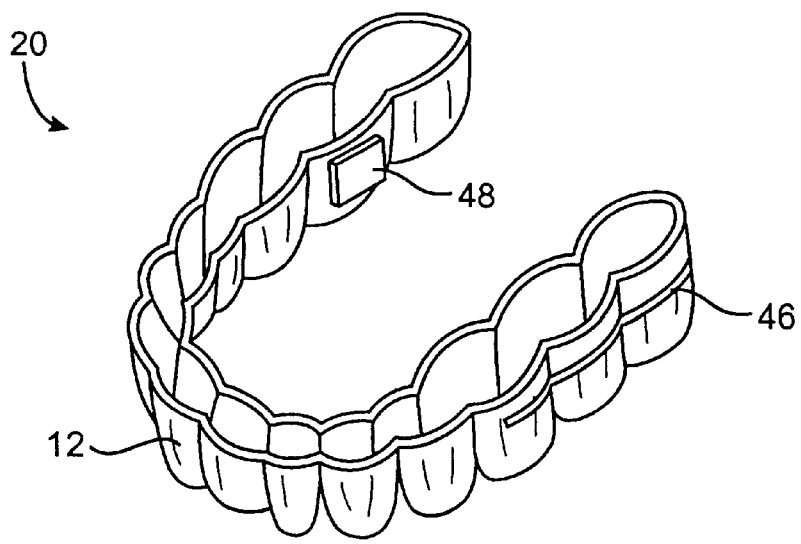
FIG. 12 depicts the use of a color or dye localized in a specific area; examples of a stripe formed in the appliance and a portion of colored material affixed to a surface are shown.

The color may be dispersed throughout the appliance, as in FIG. 11, or the color may be localized in a specific area within or on a surface of the appliance. As shown in FIG. 12, the appliance 20 may contain, for example, a stripe 46 of color or dye in a specific location. Such a stripe 46 may be visible at all times or it may only appear when removed from the oral environment. In either case, the stripe 46 may be positioned so that it is hidden from view, i.e. along the lingual surfaces or along the molars, or it may be placed anywhere along the appliance. 20. Likewise, a portion of material 48 which changes a visual characteristic may be attached, bonded or laminated to a surface of the polymer shell 12, either removably or permanently.

Methods for concurrently repositioning teeth and delivering agents to the oral environment of a patient involve the utilization of at least one tooth position adjustment appliance having a means for releasing an agent as described above. Typically, repositioning of the teeth involves placing a first repositioning appliance over the patient's teeth wherein the teeth move to a first tooth arrangement. After the teeth have moved to this arrangement, the appliance is replaced with a second repositioning appliance which is placed over the patient's teeth to move the teeth to a second tooth arrangement. This is continued with a succession of appliances until the teeth are moved to a desired arrangement. Concurrent delivery of an agent is accomplished by releasing the agent from at least one of the repositioning appliances while the appliance is in place over the patient's teeth. Means for releasing the agent may include any of the means described previously.

Figure 13:
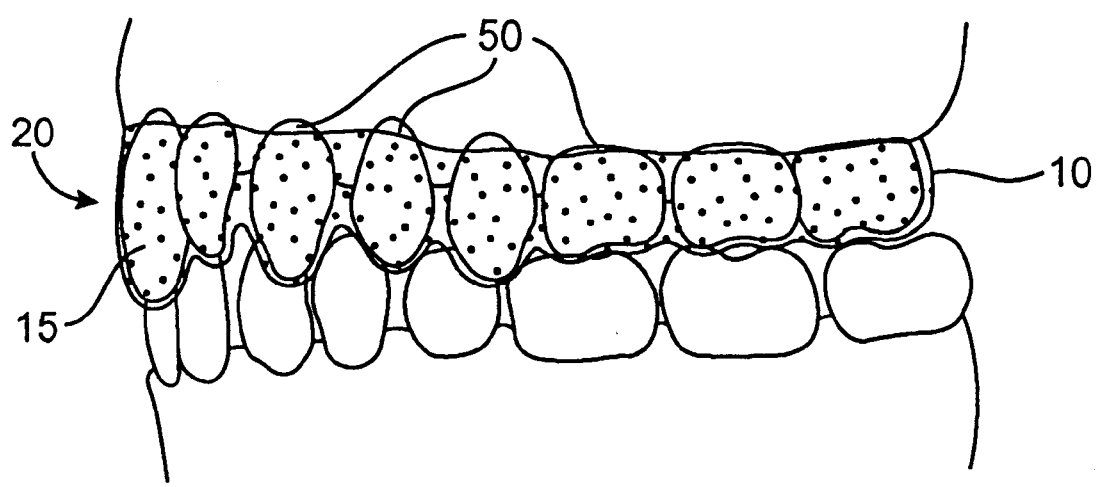
FIG. 13 illustrates the positioning of an appliance of the present invention over the teeth of the patient.

Referring to FIG. 13, simply positioning the appliance 20 over the patient's teeth 50 may deliver the agent 15 to the oral environment. It may be appreciated that the agent 15 is enlarged in FIG. 13 to illustrate the presence of the agent 15 in the appliance 20. In many cases, the dispersed agent 15 is so fine that the appliance 20 appears transparent. In other cases, the agent 15 may be present at a density high enough to be visible. When the appliance 20 is pre-loaded or pre-filled with agent 15, the appliance 20 may be removed from the packaging and immediately inserted in the patient's mouth, as shown in FIG. 13. However, appliances that are not pre-filled may require loading prior to placing over the teeth. Loading may comprise placing the agent 15 in a teeth-receiving cavity 14, as previously shown in FIG. 4. Alternatively, loading may comprise placing the agent 15 into an agent release reservoir 60, as shown in FIG. 8. Loading may also comprise adhering a rate-controlling or controlled-release material 24 containing the agent 15 to a surface of the appliance 20, as shown in FIG. 6.

Figure 14:
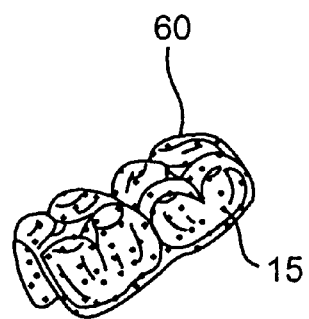
FIG. 14 is a perspective view of a pre-formed sheet 60 of material containing an agent may have a shape contoured to fit against a surface of an appliance.
Figure 15:
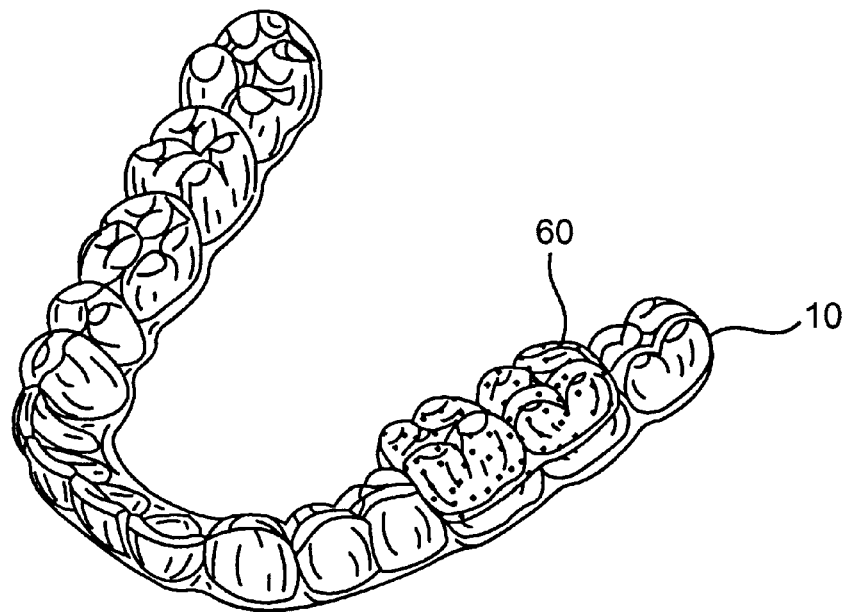
FIG. 15 is a perspective view of the pre-formed sheet of FIG. 14 fit over an outside surface of an appliance.
Figure 16:
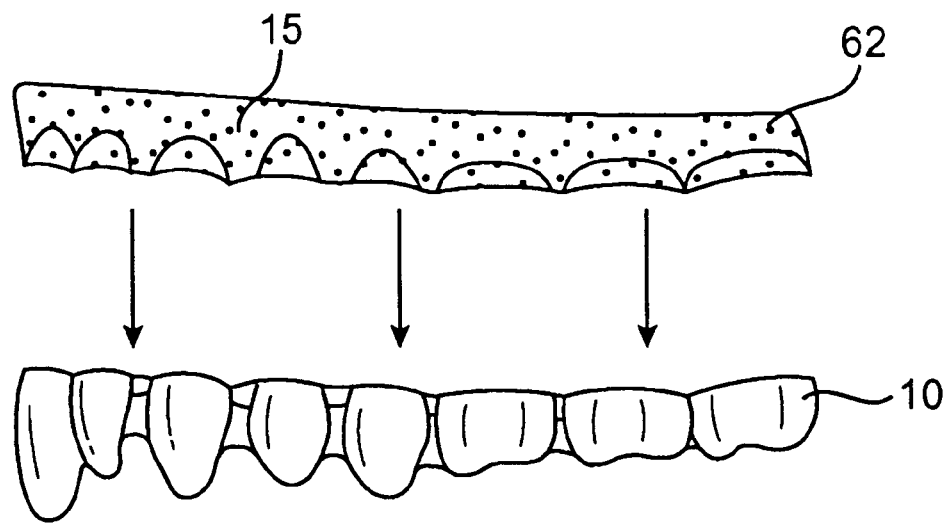
FIG. 16 is a side view of a pre-formed sheet of material containing an agent, contoured to fit against a surface of the teeth and gingiva, together with a side view of an appliance to which it may be joined.
Figure 17:
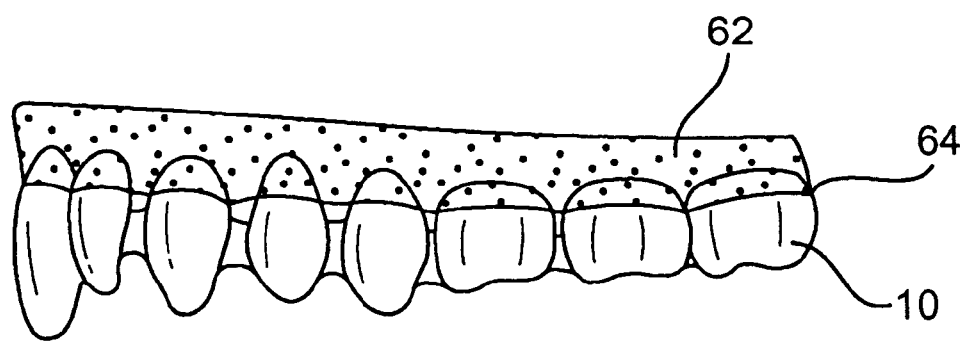
FIG. 17 is a side view of the pre-formed sheet and appliance of FIG. 16 joined with an adhesive layer.

Although some of these loading methods may require specially designed appliances, a number of these methods may be applied to any position adjustment appliance. For example, a series of repositioning appliances may be generated according to a treatment plan and provided to a patient. At any point during the treatment plan, delivery of an agent to the oral environment may be necessary or desired. The practitioner or the patient may then load the appliance with the agent or agent delivery means and continue with the treatment plan. This may be easily accomplished with the use of a strip of controlled-release material containing the agent. The strip may be adhered to any surface of the appliance with adhesive or any suitable means of attachment. Similarly, any type of agent delivery layer may be attached to the appliance for this purpose. For example, a pre-formed sheet of material encapsulating the agent may be used wherein the form comprises a shape wherein at least a portion of the shape is contoured to fit against the surface of an appliance or a surface of the teeth or gingiva. As shown in FIG. 14, the pre-formed sheet 60 of material containing the agent 15 may have a shape contoured to fit against an outside surface of the appliance 10. Shown in FIG. 15, the material 60 may be adhered to the surface with adhesive or may be press-fit to the surface and therefore held in place by compressive forces or friction. Similarly, the preformed sheet of material may have a shape contoured to fit against a surface of the teeth or gingiva. As shown in FIG. 16, the pre-formed sheet 62 containing the agent 15 may be shaped to fit against the gingival margin, thus having contours reflecting the gumline. The sheet 62 may then be joined with the appliance 10, as illustrated by the joining arrows in FIG. 16. Referring to FIG. 17, the sheet 62 and the appliance 10 may be bonded together by an adhesive layer 64 to form an appliance which provides agent delivery. the sheet 62 may be flexible to accommodate easy attachment of the sheet 62 to the appliance and positioning and removal of the appliance over the patient's teeth.

The repositioning appliances may be periodically removed for daily dental hygiene practices and other events throughout the repositioning protocol or treatment plan until the teeth are moved to at least near the desired tooth arrangement. While the appliance is removed from the teeth, the appliance may be replenished with the agent or substance for delivery. Replenishment may be performed immediately prior to each time the appliance is replaced over the teeth or it may be performed according to any prescribed protocol.

What is claimed is:

1. A system for repositioning teeth and releasing an agent to an oral environment, said system comprising:
   at least three tooth positioning appliances, wherein said appliances comprise polymeric shells having cavities, which are removably placeable over the teeth and wherein the cavities of successive shells are shaped to reposition teeth from one arrangement to a successive arrangement; and
   means coupled to sonic of the appliances and not others for releasing the agent to the oral environment when the some of the appliances are in place over the teeth and not when the others are in place so that the agent is delivered at spaced-apart times during repositioning of the teeth.

2. A system as in claim 1, wherein said releasing means comprises a layer including the agent formed over at least a portion of a surface of the appliances.

3. A system as in claim 2, wherein the surface is a cavity surface.

4. A system as in claim 2, wherein the surface is an external surface.

5. A system as in claim 2, wherein the layer consists essentially of the agent.

6. A system as in claim 2, wherein the layer comprises the agent present in or on a carrier or binder.

7. A system as in claim 2, wherein the agent is encapsulated in the layer.

8. A system as in claim 6 or 7, wherein the agent comprises the agent microencapsulated in a polymer material.

9. A system as in claim 7, wherein the layer comprises a rate controlling material wherein the rate controlling material controls the rate at which the agent is released from the layer.

10. A system as in claim 9, wherein the rate controlling material comprises a polymer matrix.

11. A system as in claim 10, wherein the agent is released from the layer by diffusion through the polymer matrix.

12. A system as in claim 10, wherein the agent is released from the layer by degradation of the polymer matrix.

13. A system as in claim 9, wherein the rate controlling material is porous and the agent is released from the material by elution from pores.

14. A system as in claim 1, wherein at least a portion of at least some of the polymeric shells are formed from a controlled release material wherein the rate controlling material controls the rate at which the agent is released from the shell.

15. A system as in claim 14, wherein the rate controlling material comprises a polymer matrix.

16. A system as in claim 15, wherein the agent is released from the layer by diffusion through the polymer matrix.

17. A system as in claim 14, wherein the rate controlling material is porous and the agent is released from the material by elution from pores.

18. A system as in claim 1, wherein said releasing means comprises a reservoir formed in the shell in addition to the cavity which receives the teeth.

19. A system as in claim 18, further comprising a rate controlling membrane disposed over the reservoir wherein the rate controlling membrane controls the rate at which the agent is released from the reservoir.

20. A system as in claim 19, wherein the reservoir is pre-filled with the agent to be released.

21. A system as in claim 19, wherein the reservoir is replenishable with the agent to be released.

22. A system as in claim 1, wherein the agent comprises a material selected from the group consisting of fluoride, an antibiotic, a bleaching material, a flavor and a scent.

23. A system as in claim 22, wherein the agent comprises at least two materials selected from the group.

24. A system as in claim 22, wherein the material is a fluoride selected from the group consisting of acidulated phosphate fluoride gel, neutral sodium fluoride, hydrogen fluoride and stannous fluoride.

25. A system as in claim 22, wherein the material is an antibiotic selected from the group consisting of tetracycline and chlorhexidine.

26. A system as in claim 22, wherein the material is carbamide peroxide.

27. A system as in claim 22, wherein the material is a flavor or scent selected from the group consisting of essential oils, natural flavorings and artificial flavorings.

28. A method for concurrently repositioning teeth and delivering agents to the oral environment of a patient, said method comprising:

placing a first tooth position adjustment appliance over the patient's teeth, wherein the teeth move to a first tooth arrangement, and placing a second tooth position adjustment appliance over the patient's teeth after the teeth have moved to the first tooth arrangement, wherein the teeth move to a second tooth arrangement;

wherein the agent is released from the first or the second tooth position adjustment appliances to the oral environment while the agent releasing appliance is in place over the patient's teeth so that the agent is delivered at spaced-apart times during repositioning of the teeth.

29. A method as in claim 28, further comprising loading the first second tooth positioning appliance with the agent prior to placing the appliance over the teeth.

30. A method as in claim 29, wherein loading comprises placing the agent in a teeth-receiving cavity in the appliance immediately prior to placing the appliance over the teeth.

31. A method as in claim 29, wherein loading comprises placing the agent into an agent release reservoir in the appliance immediately prior to placing the appliance over the teeth.

32. A method as in claim 29, wherein loading comprises adhering a rate controlling material containing the agent to a surface of the appliance prior to placing the appliance over the teeth.

33. A method as in claim 29, wherein loading comprises absorbing the agent into a porous material on or within the appliance immediately prior to placing the appliance over the teeth.

34. A method as in claim 28 wherein placing the first or second tooth position adjustment appliance comprises periodically placing and removing the appliance until the teeth are moved to at least near the first or second tooth arrangement, wherein the method further comprises replenishing the agent while the appliance is removed from the teeth and before the appliance is replaced over the teeth.

35. A method as in claim 34, wherein the appliance is replenished with the agent immediately prior to each time the appliance is replaced over the teeth.

36. A method of claim 28, wherein the first or second appliance is preloaded with the agent prior to placement over the teeth.

37. A method for introducing agent delivery to a prescribed tooth repositioning treatment plan, said method comprising:

providing at least three tooth positioning appliances, wherein said appliances comprise polymeric shells having cavities, which are removably placeable over the teeth and wherein the cavities of successive shells are shaped to reposition teeth from one arrangement to a successive arrangement according to the treatment plan; and coupling to at least one but not all of the appliances an agent which will be released to the oral environment when the at least one but not all of the appliances is in place over the teeth so that the agent is delivered at spaced-apart tunes during repositioning of the teeth.

38. A method as in claim 37, wherein the agent is incorporated in a layer and the coupling step comprises adhering the layer including the agent to at least a portion of a surface of the appliance.

39. A method as in claim 38, wherein the layer consists essentially of the agent and adhering comprises coating, spraying, dipping or painting the agent on the surface.

40. A method as in claim 38, wherein the layer comprises the agent present in or on a carrier or binder.

41. A method as in claim 38, wherein the layer comprises the agent encapsulated in the layer.

42. A method as in claim 41, wherein the layer comprises a sheet of rate controlling material wherein the rate controlling material controls the rate at which the agent is released form the layer.

43. A method as in claim 42, wherein the adhering step comprises bonding the sheet to the surface with an adhesive.

44. A method as in claim 42, wherein the adhering step comprises attaching the sheet to the surface by press fitting.

45. A method as in claim 42, wherein the sheet is pre-formed to a shape adapted for fitting against the surface of the appliance or a surface of the teeth or gingiva.

* * * * *

UNITED STATES PATENT AND TRADEMARK OFFICE
CERTIFICATE OF CORRECTION

PATENT NO. : 6,607,382 B1
DATED : August 19, 2003
INVENTOR(S) : Eric Kuo et al.

It is certified that error appears in the above-identified patent and that said Letters Patent is hereby corrected as shown below:

Column 15,
Line 59, delete "sonic" and insert therefor -- some --.

Column 17,
Line 14, delete "first second" and insert therefor -- first or second --.

Signed and Sealed this

Third Day of August, 2004

JON W. DUDAS
*Acting Director of the United States Patent and Trademark Office*